(12) United States Patent
Park et al.

(10) Patent No.: US 12,053,306 B2
(45) Date of Patent: Aug. 6, 2024

(54) APPARATUS AND METHOD FOR ESTIMATING BLOOD PRESSURE

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Youn Ho Kim, Hwaseong-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1326 days.

(21) Appl. No.: 16/415,134

(22) Filed: May 17, 2019

(65) Prior Publication Data
US 2020/0113526 A1  Apr. 16, 2020

(30) Foreign Application Priority Data
Oct. 12, 2018  (KR) .................. 10-2018-0122078

(51) Int. Cl.
*A61B 5/021* (2006.01)
*A61B 5/00* (2006.01)
(Continued)

(52) U.S. Cl.
CPC ............ *A61B 5/7278* (2013.01); *A61B 5/021* (2013.01); *A61B 5/02116* (2013.01);
(Continued)

(58) Field of Classification Search
CPC ... A61B 5/7278; A61B 5/021; A61B 5/02116; A61B 5/02125; A61B 5/029;
(Continued)

(56) References Cited

U.S. PATENT DOCUMENTS

| | | |
|---|---|---|
| 6,582,374 B2 | 6/2003 | Yokozeki |
| 8,585,605 B2 | 11/2013 | Sola I Caros et al. |

(Continued)

FOREIGN PATENT DOCUMENTS

| | | |
|---|---|---|
| JP | 3618297 B2 | 2/2005 |
| JP | 2010-246801 A | 11/2010 |

(Continued)

OTHER PUBLICATIONS

Lee J, Sohn J, Park J, Yang S, Lee S, Kim HC. Novel blood pressure and pulse pressure estimation based on pulse transit time and stroke volume approximation. Biomed Eng Online. Jun. 18, 2018;17(1):81 (Year: 2018).*

(Continued)

*Primary Examiner* — Andrey Shostak
(74) *Attorney, Agent, or Firm* — Sughrue Mion, PLLC

(57) ABSTRACT

An apparatus for estimating blood pressure is provided. According to one embodiment, the apparatus for estimating blood pressure may include a sensor configured to measure a bio-signal from a subject, and a processor configured to acquire, form the bio-signal, a first feature value associated with cardiac output (CO) and a second feature value associated with total peripheral resistance (TPR), determine whether a current mechanism of blood pressure change of the subject is a post-exercise hypotension mechanism based on the first feature value and the second feature value, and estimate blood pressure according to determination of whether the current mechanism is the post-exercise hypotension mechanism.

11 Claims, 14 Drawing Sheets

(51) Int. Cl.
  *A61B 5/029* (2006.01)
  *A61B 5/024* (2006.01)
(52) U.S. Cl.
  CPC .......... *A61B 5/02125* (2013.01); *A61B 5/029* (2013.01); *A61B 5/024* (2013.01)
(58) Field of Classification Search
  CPC ..... A61B 5/024; A61B 5/002; A61B 5/02416; A61B 5/02007; A61B 5/681; A61B 5/741; A61B 5/7455; A61B 5/02108; A61B 5/318; A61B 5/389; A61B 5/6802; A61B 5/746; G16H 50/30
  See application file for complete search history.

(56) References Cited

U.S. PATENT DOCUMENTS

| | | | |
|---|---|---|---|
| 8,591,428 | B2 | 11/2013 | Sugo |
| 2002/0099298 | A1 | 7/2002 | Yokozeki |
| 2009/0163821 | A1 | 6/2009 | Sola I Caros et al. |
| 2009/0204012 | A1 | 8/2009 | Joeken |
| 2010/0268101 | A1 | 10/2010 | Sugo |
| 2016/0038041 | A1 | 2/2016 | Clinton |
| 2016/0081563 | A1* | 3/2016 | Wiard .................. A61B 5/7278 600/485 |
| 2017/0112395 | A1 | 4/2017 | Kim et al. |
| 2018/0008200 | A1 | 1/2018 | Romesburg |

FOREIGN PATENT DOCUMENTS

| | | |
|---|---|---|
| JP | 4668421 B2 | 4/2011 |
| JP | 5330069 B2 | 10/2013 |
| KR | 10-1503604 B1 | 3/2015 |
| KR | 10-2017-0048970 A | 5/2017 |
| KR | 10-1746492 B1 | 6/2017 |
| KR | 10-2018-0077019 A | 7/2018 |
| WO | 00/47110 A1 | 8/2000 |

OTHER PUBLICATIONS

Choi, Hee-Nam et al., "The Response of Blood Pressure and Double Product After Acute Resistance Exercise on Various Breathing Methods", Korean J Health Promot Dis Prev, 2005, vol. 5, No. 4, pp. 308-314. (7 pages total).

Teng, X. F. et al., "An Evaluation of a PTT-Based Method for Noninvasive and Cuffless Estimation of Arterial Blood Pressure", Proceedings of the 28th IEEE EMBS Annual International Conference, New York City, USA, Aug. 30, 2006-Sep. 3, 2006, SaEP9.11, pp. 6049-6052, XP031236911. (4 pages total).

De Brito, Leandro C. et al., "Post-Exercise Hypotension and Its Mechanisms Differ after Morning and Evening Exercise: A Randomized Crossover Study", PLOS ONE, Jul. 17, 2015, pp. 1-16, XP055656985. (16 pages total).

Halliwill, John R. et al., "Postexercise hypotension and sustained postexercise vasodilatation: what happens after we exercise?", Experimental Physiology, vol. 98, No. 1, Oct. 9, 2012, pp. 7-18, XP055656988. (12 pages total).

Communication issued Jan. 21, 2020 by the European Patent Office in counterpart European Patent Application No. 19184920.7.

Lee et al., "Novel blood pressure and pulse pressure estimation based on pulse transit time and stroke volume approximation", BioMed Eng OnLine, Jun. 18, 2018, 20 total pages, vol. 17, doi: 10.1186/s12938-018-0510-8.

Notice of Allowance dated Feb. 21, 2024, issued by Korean Patent Office in Korean Patent Application No. 10-2018-0122078.

* cited by examiner

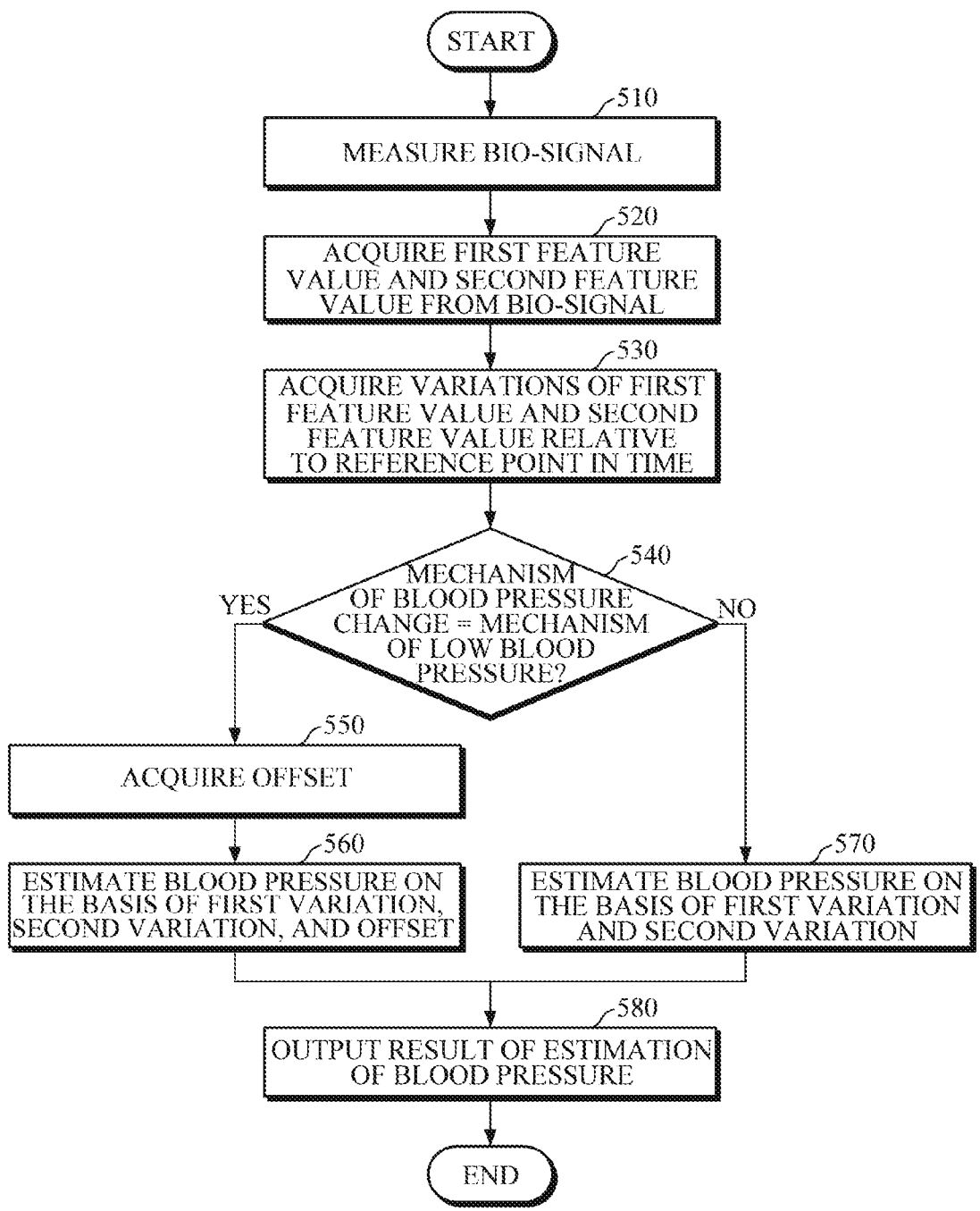

APPARATUS AND METHOD FOR ESTIMATING BLOOD PRESSURE

CROSS-REFERENCE TO RELATED APPLICATION(S)

This application is based on and claims priority under 35 USC § 119(a) of Korean Patent Application No. 10-2018-0122078, filed on Oct. 12, 2018, in the Korean Intellectual Property Office, the disclosure of which is incorporated herein by reference in its entirety.

BACKGROUND

1. Field

The following description relates to cuffless blood pressure estimation.

2. Description of Related Art

Recently, active research has been conducted on Internet technology (IT)-medical convergence technology, which is a combination of IT technology and medical technology, due to the aging population structure, rapidly growing medical expenses, and the shortage of professional medical service personnel. In particular, the monitoring of the health status of the human body is not limited to the hospital, but is expanding to the field of mobile health care, which monitors the health status of users moving in everyday life, such as home and office. Archetypal examples of bio-signals indicating the individual's health status may include an electrocardiography (ECG) signal, a photoplethysmogram (PPG) signal, an electromyography (EMG) signal, and the like. Various bio-signal sensors are being developed to measure such signals in daily life. In particular, in the case of a PPG sensor, it is possible to estimate blood pressure of a human body by analyzing pulse waveforms in which a cardiovascular status is reflected.

According to researches on PPG bio-signals, the entire PPG signal is a superposition of a propagation wave propagating from the heart to peripheral parts of a body and reflection waves returning from the peripheral parts of the body. It is known that information from which blood pressure can be estimated can be obtained by extracting various features associated with the propagation wave or the reflection waves.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, there is provided an apparatus for estimating blood pressure, the apparatus including: a sensor configured to measure a bio-signal from a subject; and a processor configured to acquire, form the bio-signal, a first feature value associated with cardiac output (CO) and a second feature value associated with total peripheral resistance (TPR), determine whether a current mechanism of blood pressure change of the subject is a post-exercise hypotension mechanism based on the first feature value and the second feature value, and estimate blood pressure according to determination of whether the current mechanism of blood pressure change is the post-exercise hypotension mechanism.

The processor may be further configured to determine whether the current mechanism of blood pressure change is the post-exercise hypotension mechanism, based on comparison between at least one of the first feature value, the second feature value, a first normalization value obtained by normalizing the first feature value, a second normalization value obtained by normalizing the second feature value, a difference between the first feature value and the second feature value, and a difference between the first normalization value and the second normalization value, and a preset threshold.

When the difference between the first normalization value and the second normalization value is greater than a first threshold, the second normalization value is smaller than a second threshold and the second feature value is smaller than a third threshold, the processor may be further configured to determine that the current mechanism of blood pressure change is the post-exercise hypotension mechanism.

When the first normalization value is greater than a fourth threshold and the second normalization value is smaller than a fifth threshold, the processor may be further configured to determine that the current mechanism of blood pressure change is the post-exercise hypotension mechanism.

When the first feature value or the first normalization value is greater than a sixth threshold, the processor may be further configured to determine that the current mechanism of blood pressure change is the post-exercise hypotension mechanism.

The processor may be further configured to obtain the first normalization value by dividing the first feature value by a first reference feature value and obtain the second normalization value by dividing the second feature value by a second reference feature value.

The first reference feature value and the second reference feature value may respectively correspond to a value associated with the CO are a value associated with the TPR, which are obtained from the bio-signal measured at a time of calibration.

The processor may be further configured to acquire the first feature value and the second feature value by using one or a combination of two or more of a heart rate, a shape of a waveform of the bio-signal, time and amplitude at a maximum point, time and amplitude at a minimum point, time and amplitude at a position of a pulse waveform component constituting the bio-signal, and an area under the waveform of the bio-signal.

The processor may be further configured to calculate a first variation of a first normalization value relative to a reference point in time and a second variation of a second normalization value relative to the reference point in time and estimate the blood pressure based on the calculated first variation and second variation, wherein the first normalization value may be obtained by normalizing the first feature value and the second normalization value is obtained by normalizing the second feature value.

In response to determining that the current mechanism of blood pressure change is not the post-exercise hypotension mechanism, the processor may be further configured to combine the first variation and the second variation and apply a blood pressure estimation formula to a result of combining the first variation and the second variation.

The processor may be further configured to combine the first variation and the second variation after adjusting at least one of the first variation and the second variation and apply a blood pressure estimation formula to a result of combining the first variation and the second variation, in response to determining that the current mechanism of blood pressure change is the post-exercise hypotension mechanism.

The processor may be further configured to adjust the first variation using an attenuation coefficient for attenuating the first variation or adjust the second variation using an amplification factor for amplifying the second variation.

When the processor adjusts the first variation using the attenuation coefficient, the processor may be further configured to calculate the attenuation coefficient based on an attenuation coefficient calculation formula that uses, as an input value, at least one of the first feature value, the second feature value, the first normalization value, the second normalization value, a difference between the first feature value and the second feature value, and a difference between the first normalization value and the second normalization value. When the processor adjusts the second variation using the amplification factor, the processor may be further configured to calculate the amplification factor based on an amplification factor calculation formula that uses, as an input value, at least one of the first feature value, the second feature value, the first normalization value, the second normalization value, a difference between the first feature value and the second feature value, and a difference between the first normalization value and the second normalization value.

The attenuation coefficient calculation formula may be a linear or nonlinear function that is defined such that the attenuation coefficient linearly or nonlinearly decreases in at least a part of an entire interval where the input value changes.

The amplification factor calculation formula may be a linear or nonlinear function that is defined such that the amplification factor linearly or nonlinearly increases in at least a part of an entire interval where the input value changes.

According to an aspect of another example embodiment, there is provided a method of estimating blood pressure, the method including: measuring a bio-signal from a subject; acquiring, from the bio-signal, a first feature value associated with cardiac output (CO) and a second feature value associated with total peripheral resistance (TPR); determining whether a current mechanism of blood pressure change of the subject is a post-exercise hypotension mechanism based on at least one of the first feature value and the second feature value; and estimating blood pressure according to determination of whether the current mechanism of blood pressure change is the post-exercise hypotension mechanism.

The determining whether the current mechanism of blood pressure change is the post-exercise hypotension mechanism may include: determining whether the current mechanism of blood pressure change is the post-exercise hypotension mechanism based on comparison between at least one of the first feature value, the second feature value, a first normalization value obtained by normalizing the first feature value, a second normalization value obtained by normalizing the second feature value, a difference between the first feature value and the second feature value, and a difference between the first normalization value and the second normalization value, and a preset threshold.

The determining whether the current mechanism of blood pressure change is the post-exercise hypotension mechanism may include: determining that the current mechanism of blood pressure change is the post-exercise hypotension mechanism when the difference between the first normalization value and the second normalization value is greater than a first threshold, the second normalization value is smaller than a second threshold and the second feature value is smaller than a third threshold.

The determining whether the current mechanism of blood pressure change is the post-exercise hypotension mechanism may include: determining that the current mechanism of blood pressure change is the post-exercise hypotension mechanism when the first normalization value is greater than a fourth threshold and the second normalization value is smaller than a fifth threshold.

The determining whether the current mechanism of blood pressure change is the post-exercise hypotension mechanism may include: determining that the current mechanism of blood pressure change is the post-exercise hypotension mechanism when the first feature value or the first normalization value is greater than a sixth threshold.

The method may further include calculating a first variation of a first normalization value relative to a reference point in time and a second variation of a second normalization value relative to the reference point in time, wherein the first normalization value may be obtained by normalizing the first feature value and the second normalization value is obtained by normalizing the second feature value.

The estimating the blood pressure may include: in response to determining that the current mechanism of blood pressure change is not the post-exercise hypotension mechanism, combining the first variation and the second variation and applying a blood pressure estimation formula to a combination result.

The estimating the blood pressure may include: in response to determining that the current mechanism of blood pressure change is the post-exercise hypotension mechanism, combining the first variation and the second variation after adjusting at least one of the first variation and the second variation and applying a blood pressure estimation formula to a combination result.

The adjusting at least one of the first variation and the second variation may include: adjusting the first variation using an attenuation coefficient for attenuating the first variation or adjusting the second variation using an amplification factor for amplifying the second variation.

According to an aspect of another example embodiment, there is provided an apparatus for estimating blood pressure, the apparatus including: a sensor configured to measure a bio-signal from a subject; and a processor configured to determine whether a current mechanism of blood pressure change of the subject is a post-exercise hypotension mechanism, according to at least one of a first feature value associated with cardiac output (CO) and a second feature value associated with total peripheral resistance (TPR) which are acquired from the bio-signal, acquire an offset value in response to determining that the current mechanism of blood pressure change is the post-exercise hypotension mechanism, and estimate blood pressure based on the first feature value, the second feature value, and the offset value.

The processor may be further configured to determine whether the current mechanism of blood pressure change is the post-exercise hypotension mechanism, based on comparison between at least one of the first feature value, the second feature value, a first normalization value obtained by normalizing the first feature value, a second normalization value obtained by normalizing the second feature value, a difference between the first feature value and the second feature value, and a difference between the first normalization value and the second normalization value, and a preset threshold.

The processor may be further configured to acquire the offset value based on at least one of a first variation of the first normalization value relative to a reference point in time, a second variation of the second normalization value relative to the reference point in time, and a variation of pulse pressure relative to the reference point in time.

In response to determining that the current mechanism of blood pressure change is not the post-exercise hypotension mechanism, the processor may be further configured to estimate the blood pressure based on a first variation of the first normalization value relative to a reference point in time and a second variation of the second normalization value relative to the reference point in time.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 5 is a flowchart illustrating a method of estimating blood pressure according to another embodiment;

Figure 1A:
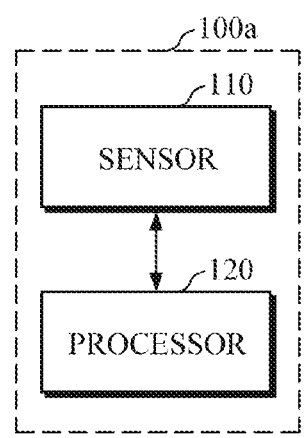
FIGS. 1A and 1B are block diagrams illustrating an apparatus for estimating blood pressure according to embodiments.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail. Throughout the drawings and the detailed description, unless otherwise described, the same drawing reference numerals will be understood to refer to the same elements, features, and structures. The relative size and depiction of these elements may be exaggerated for clarity, illustration, and convenience.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof. In addition, terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Figure 1B:
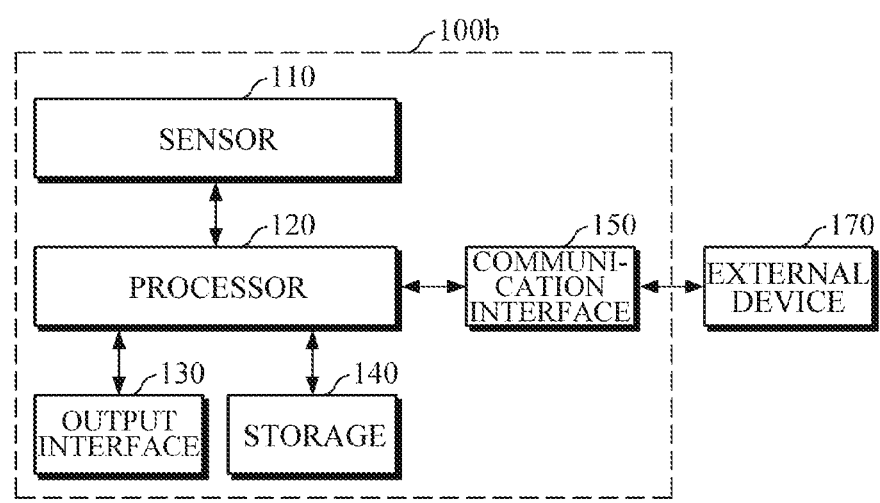

FIGS. 1A and 1B are block diagrams illustrating an apparatus for estimating blood pressure according to embodiments. The apparatuses 100a and 100b for estimating blood pressure according to the embodiments may each be mounted in a terminal, such as a smartphone, a tablet personal computer (PC), a desktop PC, a notebook PC, and the like, or a wearable device in a form which can be worn on an object of interest. In this case, the wearable device may be implemented as a wristwatch type, a bracelet type, a wrist band type, a ring type, a spectacle type, or a hairband type, but is not limited thereto. In addition, the apparatuses may be mounted in medical devices manufactured for use in measuring and analyzing bio-information in medical institutions.

Referring to FIGS. 1A and 1B, each of the apparatuses 100a and 100b includes a sensor 110 and a processor 120.

The sensor 110 may measure a bio-signal from an object of interest. In this case, the bio-signal may be a pulse wave signal including a photoplethysmogram (PPG) signal. However, the bio-signal is not limited to the pulse wave signal, and may include various bio-signals, such as an electrocardiography (ECG) signal, a PPG signal, and an electromyography (EMG) signal, which can be modeled as a summation of a plurality of waveform components. The object of interest may be a human body area that is in contact with or adjacent to the sensor 110 and is easy to measure a pulse wave. For example, the object of interest may include a wrist skin area adjacent to a radial artery and a human body skin area where capillaries or venous blood vessels pass. However, the object of interest is not limited to the above examples and may be a peripheral part of a human body, such as a finger, a toe, or the like, which is a region having a high density of blood vessels in the human body.

The sensor 110 may include a light source and a detector. The light source may emit light to the object of interest, and the detector may detect light scattered or reflected from the object of interest. The light source may include a light emitting diode (LED), a laser diode, and a phosphor and may be configured as one or two or more arrays. The detector may include one or more pixels and each pixel may include, but not limited to, a photodiode, a photo transistor, and an image sensor, each of which detects light and converts the light into an electrical signal.

The processor 120 may be electrically connected to the sensor 110. The processor 120 may control the sensor 110 in response to a request for estimation of blood pressure from the processor 120 and receive a bio-signal from the sensor 110. The request for estimation of blood pressure may be input by a user or may occur when a predetermined cycle is reached. The processor 120 may perform preprocessing, such as filtering for removing noise, amplification of a bio-signal, or conversion of a bio-signal into a digital signal, when an electrical bio-signal is received from the sensor 110.

The processor 120 may estimate blood pressure based on the bio-signal received from the sensor 110. The processor 120 may determine mechanism of blood pressure change by analyzing a waveform of the bio-signal and estimate blood pressure by adaptively applying a blood pressure estimation formula according to the determined mechanism of blood pressure change. In this case, the mechanism of blood pressure change may include general mechanism of blood pressure change and mechanism of low blood pressure. The general mechanism of blood pressure change may refer to a condition in which blood pressure increases as cardiac output (CO) increases. The general mechanism of blood pressure may occur while a subject is in a resting state, a non-exercising state, or a mild-exercising state. The mechanism of low blood pressure may refer to a condition in which blood pressure is not increased and hypotension occurs even when cardiac output increases. The mechanism of low blood pressure may occur during high-intensity aerobic exercise or a certain resting period following high-intensity aerobic exercise. The mechanism of low blood pressure may be also referred to as a post-exercise hypotension mechanism. In estimating blood pressure, different methods may be applied to the same CO value, depending on whether the subject is in the general blood pressure mechanism or the post-exercise hypotension mechanism.

For example, the processor 120 may acquire feature values associated with CO and/or total peripheral resistance (TPR) and determine the mechanism of blood pressure change using the acquired feature values. Here, the feature value associated with CO may be a feature value that has a tendency of increasing or decreasing proportionally to the CO when the CO is relatively greatly increased or decreased compared to the TPR that does not significantly change relative to a stable state. Similarly, the feature value associated with the TPR may be a feature value that has a tendency of increasing or decreasing proportionally to the TPR when the TPR is relatively greatly increased or decreased compared to the CO that does not significantly change relative to a stable state. The processor 120 may compare the acquired feature values or values calculated based on the feature values with preset thresholds and determine whether the mechanism of blood pressure change at a current point in time at which to measure blood pressure is a general mechanism of blood pressure change or a mechanism of low blood pressure.

Referring to FIG. 1B, the apparatus 100*b* for estimating blood pressure may further include an output interface 130, a storage 140, and a communication interface 150.

The output interface 130 may output processing results of the sensor 110 and the processor 120. For example, the output interface 130 may visually output an estimated blood pressure value through a display. Alternatively, the output interface 130 may output the estimated blood pressure value through a speaker or a haptic motor in a nonvisual method, such as voice, vibration, tactile sensation, or the like. The output interface 130 may divide an area of the display into two or more regions, output a bio-signal graph used in estimating blood pressure to a first region, and output the blood pressure estimation history in the form of a graph or the like to a second region. In particular, when the estimated blood pressure value is out of a normal range, warning information may also be output in various ways, such as being emphasized in red color, being displayed with the normal range, being output as a voice warning message, or intensity-controlled vibration, and the like.

The storage 140 may store processing results of the sensor 110 and the processor 120. In addition, the storage 140 may store a variety of reference information for blood pressure estimation. For example, the reference information may include user characteristic information, such as age, sex, health status, or the like. In addition, the reference information may include information on reference blood pressure, a blood pressure estimation model, a blood pressure estimation cycle, an attenuation coefficient calculation formula, an amplification factor calculation formula, various thresholds for determining mechanism of blood pressure change, a criterion for determining mechanism of blood pressure change, a method of estimating blood pressure in the case of mechanism of low blood pressure, and the like. However, the reference information is not limited to the above examples.

The storage 140 may include a storage medium, such as a memory of flash memory type, hard disk type, multimedia card micro type, or card type (e.g., SD or XD memory), random access memory (RAM), static random access memory (SRAM), read-only memory (ROM), electrically erasable programmable read-only memory (EEPROM), programmable read-only memory (PROM), magnetic memory, magnetic disk, optical disk, or the like, but is not limited thereto.

The communication interface 150 may communicate with an external device 170 using wired/wireless communication technologies under the control of the processor 120 and transmit and receive a variety of data. For example, the communication interface 150 may transmit a blood pressure estimation result to the external device 170 and receive various pieces of reference information to estimate blood pressure from the external device 170. The external device 170 may include an information processing device, such as a cuff-type blood pressure measurement device, a smartphone, a tablet PC, a desktop PC, a laptop PC, or the like.

The communication technology may include Bluetooth communication, Bluetooth low energy (BLE) communication, near field communication (NFC), a wireless local area network (WLAN) communication, ZigBee communication, infrared data association (IrDA) communication, Wi-Fi direct (WFD) communication, ultra-wideband (UWB) communication, Ant+ communication, WiFi communication, radio frequency identification (RFID) communication, $3^{rd}$ generation (3G) communication, 4G communication, 5G communication, etc. However, the communication technology is not limited to the above examples.

Figure 2A:
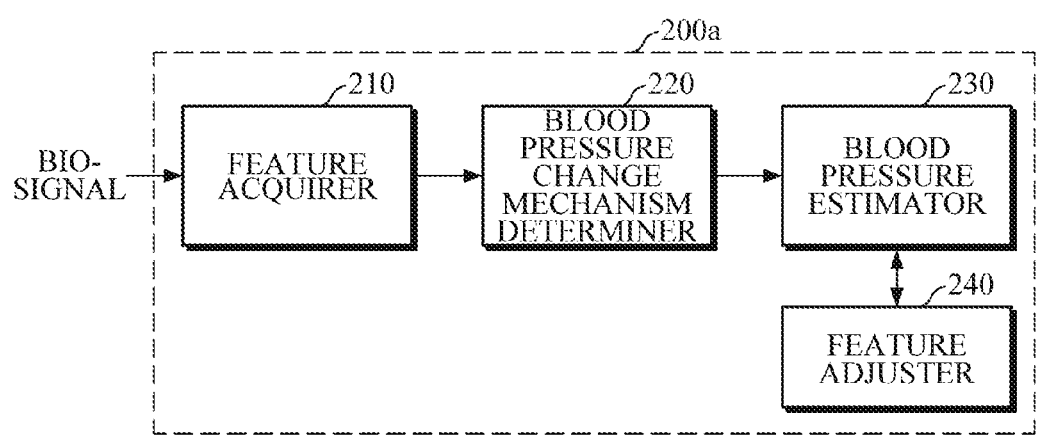
FIGS. 2A and 2B are block diagrams of the processor in accordance with the embodiments illustrated in FIGS. 1A and 1B.
Figure 2B:
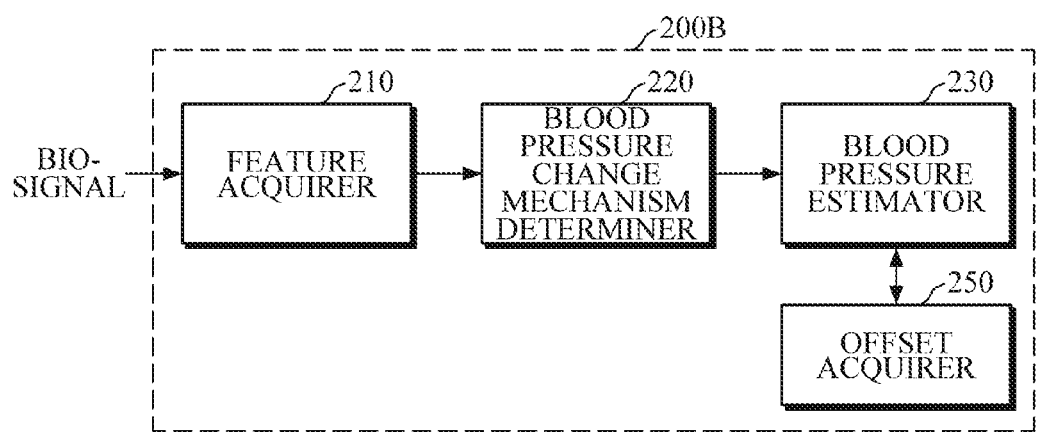

FIGS. 2A and 2B are block diagrams of the processor in accordance with the embodiments illustrated in FIGS. 1A and 1B. FIGS. 3A to 3E are graphs for describing feature extraction for estimating systolic blood pressure and diastolic blood pressure.

Referring to FIG. 2A, a processor 200*a* may include a feature acquirer 210, a blood pressure change mechanism determiner 220, a blood pressure estimator 230, and a feature adjuster 240.

Figure 3A:
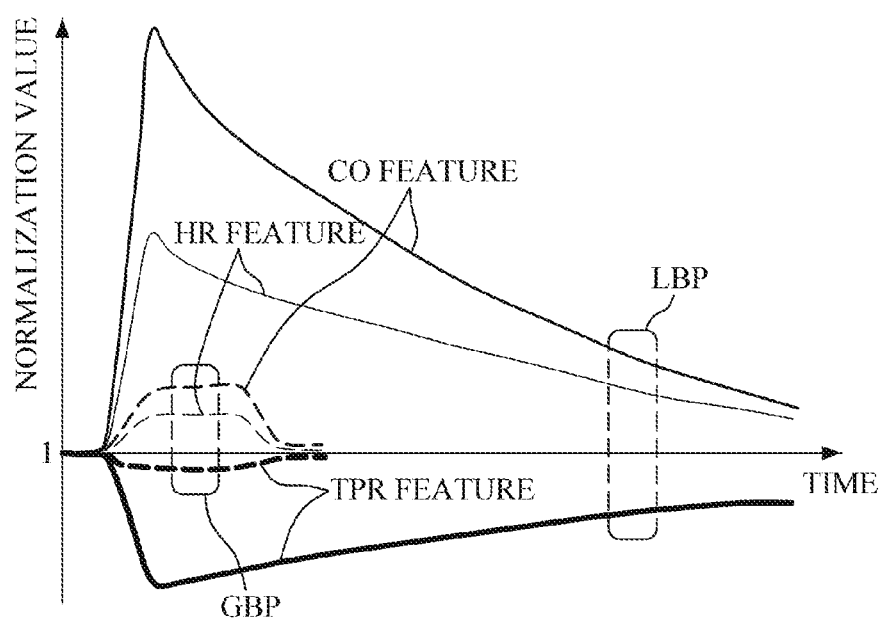
FIGS. 3A, 3B, 3C, 3D, and 3E are graphs for describing feature extraction for estimating systolic blood pressure and diastolic blood pressure.

Since blood pressure tends to increase when the cardiac output (CO) and/or the TPR increase, the blood pressure may be estimated by extracting a CO-associated feature value and a TPR-associated feature value, from a bio-signal. Referring to FIG. 3A, in a general mechanism of blood pressure change (GBP), actual blood pressure increases when the CO increases. On the other hand, in a case where blood pressure changes after exercise, mechanism of low blood pressure (LBP) may be activated in which actual blood pressure is lowered even when the CO increases. In the present embodiment, blood pressure is estimated in consideration of various situations in which blood pressure changes so that it is possible to accurately estimate blood pressure according to the mechanism of blood pressure change.

The feature acquirer 210 may acquire a feature value by analyzing a bio-signal received from the sensor 110. In particular, the feature value may include a first feature value associated with CO and a second feature value associated with TPR.

For example, the feature acquirer 210 may acquire the first feature value and the second feature value by using one or a combination of two or more of a shape of a waveform, time and amplitude at a maximum point, time and amplitude at a minimum point, time and amplitude at a position of a pulse waveform component of the bio-signal, and the area under the waveform of the bio-signal within a certain time period. In this case, the combination may be made in various ways, such as addition, subtraction, division, multiplication, log value, and a combination thereof, and is not particularly limited to any specific way. For example, a heart rate (HR) may be used as the first feature value and an amplitude ratio of pulse waveform components constituting the entire bio-signal may be used as the second feature value. However, the feature values are not limited to the above examples. In this case, the feature acquirer 210 may obtain a second-order derivative of the bio-signal in order to obtain a position of the pulse waveform component constituting the bio-signal and may determine a position of a minimum point and/or a maximum point as the position of the pulse waveform component by searching for the minimum point and/or the maximum point of the second-order derivative signal.

The blood pressure change mechanism determiner 220 may determine a mechanism of blood pressure change using the first feature value and/or the second feature value. In one example, the blood pressure change mechanism determiner 220 may compare at least one of the first feature value, the second feature value, and a difference between the first and second feature values with a preset threshold and determine the mechanism of blood pressure change based on the comparison result. In another example, the first feature value and the second feature value may be normalized to obtain a first normalization value and a second normalization value, respectively, and may compare at least one of the first normalization value, the second normalization value, and a difference between the first and second normalization values with a preset threshold. Other modifications may be made. In this case, the first normalization value and the second normalization value may be obtained by dividing the first feature value and the second feature value by a first reference feature value and a second reference feature value at a time of calibration, respectively.

For example, when the difference between the first normalization value and the second normalization value is greater than a first threshold, the second normalization value is smaller than a second threshold and the second feature value is smaller than a third threshold, the mechanism of blood pressure change may be determined to be the mechanism of low blood pressure, and otherwise, may be determined to be the general mechanism of blood pressure change. Alternatively, when the first normalization value is greater than a fourth threshold and the second normalization value is smaller than a fifth threshold, the mechanism of blood pressure change may be determined to be the mechanism of low blood pressure, and otherwise, may be determined to be the general mechanism of blood pressure change. Alternatively, when the first feature value or the first normalization value is greater than a preset sixth threshold, it may be determined that the mechanism of low blood pressure occurs. However, the embodiment is not limited to the above examples and various modifications may be possible according to the user characteristic, computing performance of a device employed, or the like. In addition, each threshold may be a value that is appropriately set through preprocessing procedures and may be a value tailored to each user or a value set for each of predetermined groups. Additionally, the thresholds may be set in advance in accordance with each device in consideration of distribution characteristics of bio-signals acquired from each device.

The blood pressure estimator 230 may estimate blood pressure according to the determined mechanism of blood pressure change. The blood pressure estimator 230 may calculate a first variation of the first normalization value relative to a reference point in time, (e.g., the time of calibration), and calculate a second variation of the second normalization value relative to the reference point in time. For example, the first variation may indicate a change in the first normalization value during a time period from an initial calibration time to an a current time which is subsequent to the initial calibration time, and the second variation may indicate a change in the second normalization value during the same time period. Below is Equation 1 which shows an example of calculation of the first variation and the second variation.

$$\Delta f_1 = \frac{f_{1cur}}{f_{1cal}} - 1 \qquad (1)$$

$$\Delta f_2 = \frac{f_{2cur}}{f_{2cal}} - 1$$

Here, $\Delta f_1$ denotes a first variation, $f_{1cur}$ denotes a first feature value, $f_{1cal}$ denotes a first reference feature value, $\Delta f_2$ denotes a second variation, $f_{2cur}$ denotes a second feature value, and $f_{2cal}$ denotes a second reference feature value.

When the determined mechanism of blood pressure change is the general mechanism of blood pressure change, the blood pressure estimator 230 may estimate blood pressure by combining the first variation and the second variation and applying a blood pressure estimation formula to the combination result. For example, a blood pressure estimation formula as shown in Equation 2 below may be used. The blood pressure estimation formula shown in Equation 2 is expressed as a linear function, but is not limited thereto.

$$BP = A(\Delta f_1 + \Delta f_2) = B \qquad (2)$$

Here, BP denotes estimated blood pressure, $\Delta f_1$ denotes a first variation, and $\Delta f_2$ denotes a second variation. In addition, A and B are predefined values, wherein A is a scale factor for scaling the value obtained by combining the first variation and the second variation and B is reference blood pressure at the time of calibration and may be, for example, actual blood pressure measured using a cuff blood pressure device or the like.

When the determined mechanism of blood pressure change is the mechanism of low blood pressure, the blood pressure estimator 230 may cause the feature adjuster 240 to adjust the first variation and/or the second variation and may estimate blood pressure using the adjusted first variation and/or second variation.

The feature adjuster 240 may attenuate the first variation using an attenuation coefficient for attenuating the first variation. In addition, the feature adjuster 240 may amplify the second variation using an amplification factor for amplifying the second variation. In this case, both or either of the attenuation of the first variation and the amplification of the second variation may be performed according to settings. That is, the first variation associated with CO is reduced using the attenuation coefficient and the second variation associated with TPR is amplified using the amplification factor so that the estimated blood pressure can be reduced in accordance with the mechanism of low blood pressure.

For example, the feature adjuster 240 may calculate the attenuation coefficient using an attenuation coefficient formula. In addition, the feature adjuster 240 may calculate the amplification factor using an amplification factor calculation formula. In this case, the attenuation coefficient calculation formula and the amplification factor calculation formula may be defined in advance and may be liner or nonlinear functions which have, as an input value, at least one of the first feature value, the second feature value, the first normalization value, the second normalization value, the difference between the first and second feature values, the difference between the first and second normalization values, and the heart rate.

Figure 3B:
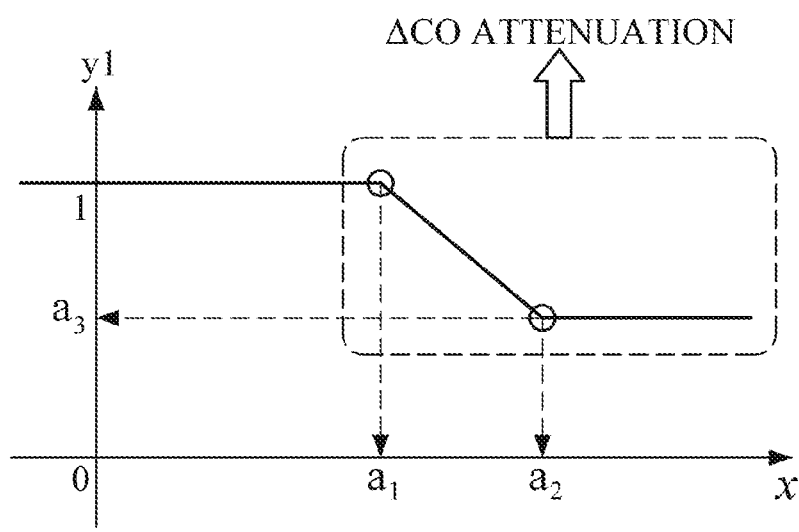
Figure 3C:
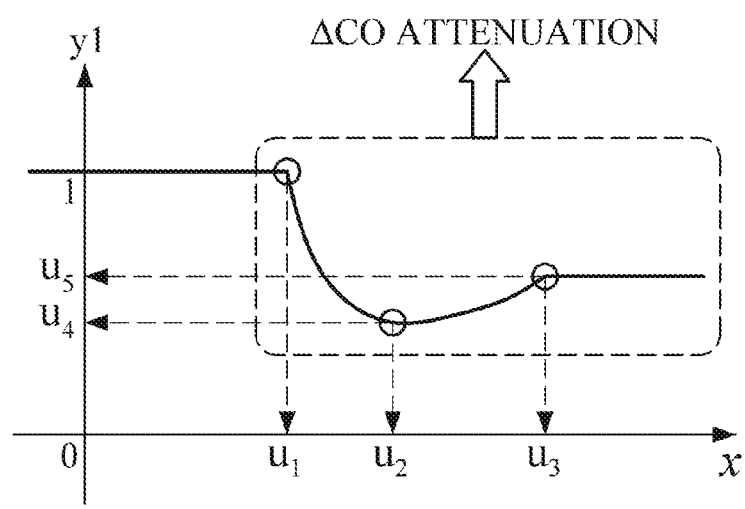

Referring to FIGS. 3B and 3C, the attenuation coefficient calculation formula may be defined such that the attenuation coefficient decreases linearly or nonlinearly in at least a part of the entire interval where the input value changes. In one example, referring to FIG. 3B, the attenuation coefficient calculation formula may set the attenuation coefficient $y_1$ to 1 in an interval from 0 to time $a_1$ in the time domain of an x-axis so that the first variation is not changed, may set the attenuation coefficient $y_1$ to be a linear function in an interval from time $a_1$ to time $a_2$ so that the first variation is reduced linearly during that interval, and may fix the attenuation coefficient $y_1$ to $a_3$, starting from time $a_2$ so that the first variation is not further reduced. According to FIG. 3B, the attenuation coefficient $y_1$ may have constant values before time $a_1$ and after time $a_2$, and may gradually decrease during the time period between time $a_1$ to time $a_2$. In another example, referring to FIG. 3C, the attenuation coefficient calculation formula may set the attenuation coefficient $y_1$ to 1 in an interval from 0 to $u_1$ in the time domain of an x-axis so that the first variation is not reduced, may define the attenuation coefficient y1 as a nonlinear function in an interval from time $u_1$ to time $u_3$ such that the attenuation coefficient $y_1$ has 1, $u_4$, and $u_5$, respectively, at time $u_1$, time $u_2$, and time $u_3$, while the first variation is reduced nonlinearly, and may fix the attenuation coefficient $y_1$ to $u_5$, starting from time $u_3$ so that the first variation is not further reduced. During the time period from time $u_1$ and time $u_3$, the attenuation coefficient calculation formula may be expressed as a parabola that is opened upwards and has a vertex (minimum point) at time $u_2$.

Figure 3D:
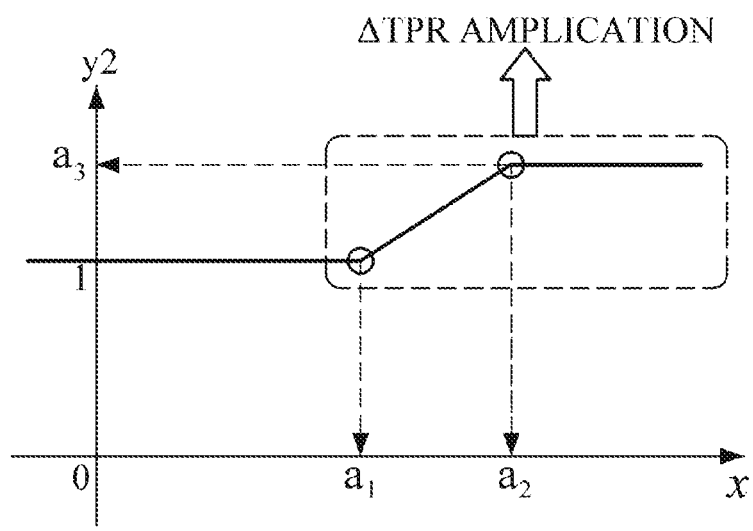
Figure 3E:
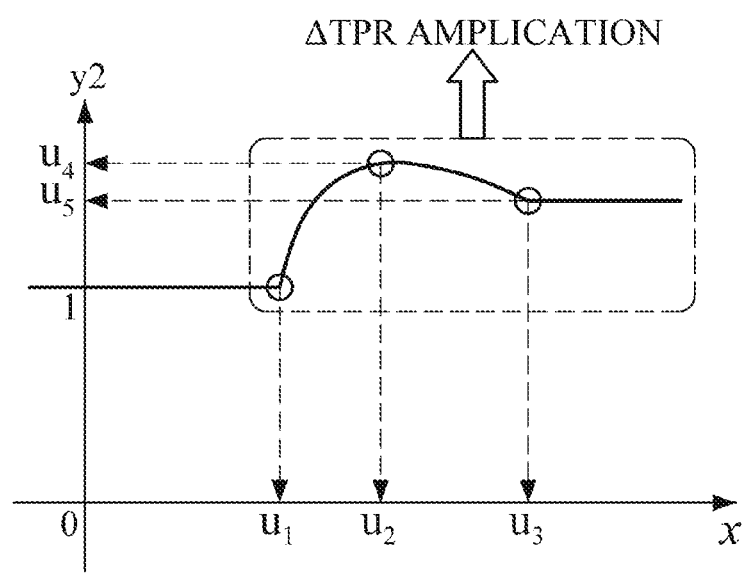

Similarly, referring to FIGS. 3D and 3E, the amplification factor calculation formula may be defined as a linear function or a nonlinear function such that the amplification factor increases linearly or nonlinearly in at least a part of the entire interval (x-axis) where an input value changes. That is, as shown in FIG. 3D, the amplification factor $y_2$ may be set to 1 in an interval from 0 to time $a_1$ in an x-axis such that the second variation does not change, may be defined as a linear function in an interval from time $a_1$ to time $a_2$ such that the second variation is increased linearly, and may be fixed to $a_3$, starting from time $a_2$ so that the second variation is not further increased. In addition, as shown in FIG. 3E, the amplification factor calculation formula may set the amplification factor $y_1$ to 1 in an interval from 0 to time $u_1$ such that the second variation does not change, may define the amplification factor $y_2$ as a nonlinear function in an interval from $u_1$ to $u_3$ such that the amplification factor $y_2$ has 1, $u_4$, and $u_5$, respectively, at time $u_1$, time $u_2$, and time $u_3$, while the second variation is nonlinearly increased, and may fix the amplification factor $y_2$ to $u_5$, starting from time $u_3$ such that the second variation is not further increased.

When the feature adjuster 240 adjusts the first variation and/or the second variation, the blood pressure estimator 230 may estimate blood pressure using a blood pressure estimation formula as shown in Equation 3.

$$BP = A(y_1 \Delta f_1 + y_2 \Delta f_2) \quad (3)$$

Here, BP denotes estimated blood pressure, $\Delta f_1$ denotes a first variation, and $\Delta f_2$ denotes a second variation. In addition, A and B are predefined values, wherein A is a scale factor for scaling the value obtained by combining the first variation and the second variation and B is reference blood pressure at the time of calibration and may be, for example, actual blood pressure measured using a cuff blood pressure device or the like. $y_1$ and $y_2$ denote, respectively, the attenuation coefficient and the amplification factor that are calculated by the feature adjuster 240.

Meanwhile, referring to 2B, the processor 200b according to another embodiment may further include an offset acquirer 250, instead of the feature adjuster 240.

According to the present embodiment, when the determined mechanism of blood pressure change is the mechanism of low blood pressure, the blood pressure estimator 230 may request the offset acquirer 250 to acquire an offset value to be further reflected in estimation of blood pressure. In this case, the offset value may be a value for correcting an error between actual blood pressure and estimated blood pressure, which may occur when the blood pressure is estimated using a blood pressure estimation formula, such as Equation 1, in the mechanism of low blood pressure.

The offset acquirer 250 may acquire the offset value using an additional feature value obtained from a bio-signal, the first variation, the second variation, a variation relative to a reference point in time of pulse pressure, and the like. For example, a third variation may be obtained by multiplying the first variation and the second variation and the offset value may be acquired using the third variation. Alternatively, an HR obtained by analyzing pulse transit time (PTT) or heart rate variation (HRV) of the measured bio-signal may be used as a feature value associated with the pulse pressure. For example, the feature value associated with the pulse pressure may be normalized to a feature value associated with pulse pressure at the time of calibration to calculate a fourth variation relative to the time of calibration and the offset value may be acquired using the calculated fourth variation. However, the embodiment is not limited to the above examples and various values that can reflect the change of actual blood pressure in the mechanism of low blood pressure may be acquired as the offset values.

The offset acquirer 250 may acquire the third variation or the fourth variation intact as the offset value. Alternatively, when there is a predefined offset estimation model, the offset acquirer 250 may input the third variation or the fourth variation to the offset estimation model and acquire a value output from the offset estimation model as the offset value. In this case, the offset estimation model may be defined in advance in consideration of various measurement conditions, such as computing performance of the apparatus for estimating blood pressure, a type of a bio-signal measurement sensor mounted in the apparatus, user characteristics, and the like.

When the offset acquirer 250 acquires the offset value that can reflect a blood pressure change situation in which the mechanism of low blood pressure is activated, the blood pressure estimator 230 may estimate blood pressure using a blood pressure estimation formula as shown in Equation 4 below.

$$BP = A(\Delta f_1 + \Delta f_2 + \text{Offset}) + B \quad (4)$$

Here, BP denotes estimated blood pressure, $\Delta f_1$ denotes a first variation, and $\Delta f_2$ denotes a second variation. In addition, A and B are predefined values, wherein A is a scale factor for scaling the value obtained by combining the first variation and the second variation and B is reference blood pressure at the time of calibration and may be, for example, actual blood pressure measured using a cuff blood pressure device or the like. Offset may be an offset value acquired by the offset acquirer 250.

Referring back to FIGS. 2A and 2B, the blood pressure estimator 230 may independently estimate mean blood pressure, diastolic blood pressure, and systolic blood pressure using the blood pressure estimation formulas shown in Equations 2 to 4. To this end, A in Equations 2 to 4 may be set to an appropriate value for the mean blood pressure, the diastolic blood pressure, and the systolic blood pressure. Alternatively, an appropriate weight may be applied to each variation in Equations 2 to 4 according to the type of blood pressure and then the weighted variations may be combined so that the mean blood pressure, the diastolic blood pressure, and the systolic blood pressure may be independently estimated.

Alternatively, the blood pressure estimator 230 may sequentially estimate the mean blood pressure, the diastolic blood pressure, and the systolic blood pressure. For example, the blood pressure estimator 230 may estimate the mean blood pressure using the above Equations 2 to 4 and estimate the diastolic blood pressure and the systolic blood pressure using the estimated mean blood pressure and the pulse pressure as shown in Equations 5 and 6 below.

$$DBP = MAP - \frac{PP}{3} \quad (5)$$

$$DBP = MAP - 0.01 \times \exp\left(4.14 - \frac{40.74}{HR}\right) \times PP$$

$$SBP = DBP + PP \quad (6)$$

Here, MAP denotes estimated mean blood pressure, DBP denotes diastolic blood pressure, and SBP denotes systolic blood pressure. In addition, PP denotes pulse pressure and HR denotes a heart rate.

Figure 4:
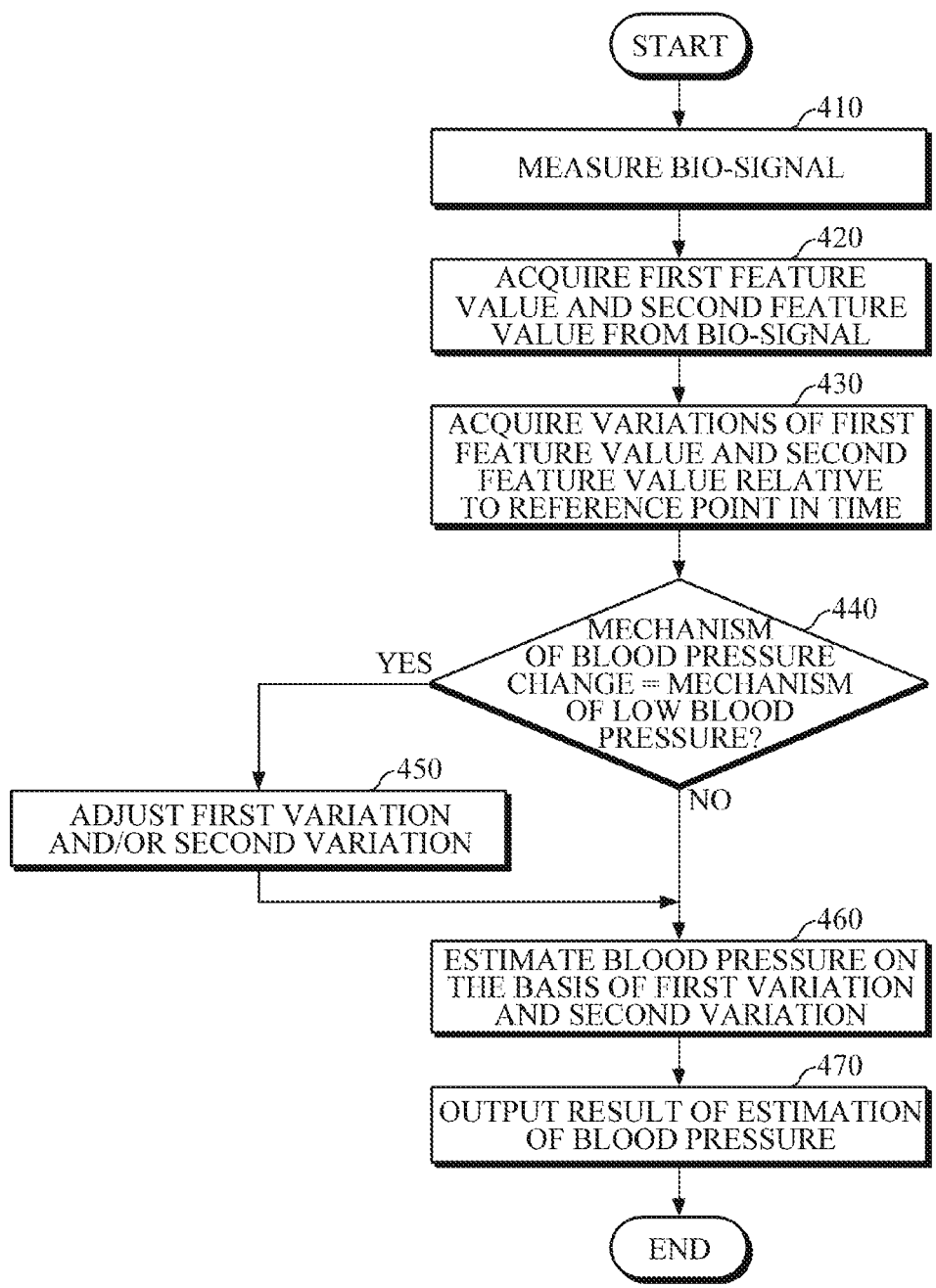
FIG. 4 is a flowchart illustrating a method of estimating blood pressure according to one embodiment.

FIG. 4 is a flowchart illustrating a method of estimating blood pressure according to one embodiment. The embodiment shown in FIG. 4 may be one example of a blood pressure estimation method performed by the apparatus 100a or 100b of FIG. 1A or 1B.

When the apparatus 100a, 100b receives a request for estimation of blood pressure, the apparatus 100a, 100b may measure a bio-signal in operation 410. The apparatus 100a, 100b may provide an interface for various interactions with a user. The user may request the estimation of blood pressure through the interface provided by the apparatus 100a, 100b. Alternatively, the apparatus 100a, 100b may receive a request for estimation of blood pressure from an external device. In this case, the request for estimation of blood pressure received from the external device may include a request for provision of a blood pressure estimation result.

When the external device is equipped with a blood pressure estimation algorithm, the request for estimation of blood pressure may include a request for provision of acquired features. The external device may include a smartphone carried by the user, a tablet PC, a laptop PC, and a wearable device. The apparatus 100a, 100b may control the sensor to measure a bio-signal including a pulse wave signal from an object of interest.

Then, a first feature value associated with CO and a second feature value associated with TPR may be acquired by analyzing the bio-signal in operation 420. For example, a heart rate may be used as the first feature value and an amplitude ratio of pulse waveform components constituting the bio-signal may be used as the second feature value. However, the first feature value and the second feature value are not limited to the above examples and a value obtained from one or a combination of two or more of time/amplitude at minimum/maximum points of the bio-signal, time/amplitude at a position of each constituent pulse waveform, the area under the waveform of the bio-signal, the heart rate may be used. In this case, a method of combining two or more features is not particularly limited.

Then, a variation of the first feature value relative to a reference point in time and a variation of the second feature value relative to the reference point in time may be obtained in operation 430. For example, a first normalization value may be obtained by dividing the first feature value that is obtained from the bio-signal at time T2, by a first reference feature value that is obtained from the bio-signal at time T1 corresponding to the time of calibration. A first variation may be calculated using the calculated first normalization value. In addition, a second normalization value may be obtained by dividing the second feature value that is obtained from the bio-signal at time T2, by a second reference feature value at the time of calibration. A second variation may be calculated using the calculated second normalization value.

A mechanism of blood pressure change may be determined in operation 440. At this time, the first feature value and the second feature value may be used without modifications or corrections, or the first normalization value obtained by normalizing the first feature value and the second normalization value obtained by normalizing the second feature value may be used. Alternatively, a new value may be obtained by combining the aforementioned values and the obtained new value may be used. For example, each of two or more values may be compared with a threshold set for each value, and when the comparison results satisfy all requirements, the mechanism of low blood pressure may be determined. Alternatively, any one of the values may be compared with a threshold to determine whether the mechanism of blood pressure change is the mechanism of low blood pressure, which is described in detail above.

Then, when the mechanism of low blood pressure is determined in operation 440, the first variation and/or the second variation may be adjusted in operation 450. In this case, the first variation may be attenuated using an attenuation coefficient or the second variation may be amplified using an amplification factor. The attenuation coefficient and the amplification factor may be obtained using preset calculation formulas as described above. Both or either of the attenuation of the first variation and the amplification of the second variation may be performed.

Then, when the first variation or the second variation is adjusted in operation 450, blood pressure may be estimated using the adjusted first variation or second variation in operation 460. When it is determined in operation 440 that the mechanism of blood pressure change is a general mechanism of blood pressure change, blood pressure may be estimated using the first variation and the second variation intact without adjusting the first and second variations in operation 460. A detailed description of operation 460 is provided above and hence is omitted.

Then, a blood pressure estimation result may be output in operation 470. For example, the blood pressure estimation result may be output through a visual output means, such as a display, using various visual methods. Alternatively, the blood pressure estimation result may be provided to the user through a speaker and/or a haptic motor using non-visual methods, such as voice, tactile sensation, vibration, and the like. In addition, a health status of the user may be determined based on estimated bio-information and warning or actions to take may be informed to the user according to the determination result.

FIG. 5 is a flowchart illustrating a method of estimating blood pressure according to another embodiment. The embodiment shown in FIG. 5 may be one embodiment of a blood pressure estimation method performed by the apparatus for estimating blood pressure 100a or 100b of FIG. 1A or 1B.

First, when the apparatus 100a, 100b receives a request for estimation of blood pressure, and the apparatus 100a, 100b may measure a bio-signal in operation 510 and acquire a first feature value associated with CO and a second feature value associated with TPR in operation 520.

Then, a variation of the first feature value relative to a reference point in time and a variation of the second feature value relative to the reference point in time may be acquired in operation 530. The variation of the first feature value may indicate a change in the first feature value during a time period between the referent point in time and a current time. The current time may be a time at which the first feature value is extracted from the bio-signal, and which is subsequent to the reference point in time. The variation of the second feature value may indicate a change in the second feature value during the time period between the reference point in time and the current time. A mechanism of blood pressure change may be determined based on the variation of the first feature value and the variation of the second feature value in operation 540.

Then, when the mechanism of blood pressure change is determined to be a mechanism of low blood pressure in operation 540, an offset for correcting an error between estimated blood pressure and actual blood pressure is acquired using the first variation and the second variation in a blood pressure change situation where the mechanism of low blood pressure is activated in operation 550. Blood pressure may be estimated using the first variation, the second variation, and the offset in operation 560. For example, the offset may be acquired using the product of the first variation and the second variation and a feature value associated with pulse pressure obtained from the bio-signal, for example, a heart rate. In this case, a predefined offset estimation model may be utilized.

When it is determined in operation 540 that the mechanism of blood pressure change is a general mechanism of blood pressure change, an additional offset may not be acquired and blood pressure may be estimated using the first variation and the second variation in operation 570.

Then, the blood pressure estimation result may be output in operation 580. For example, the blood pressure estimation result may be provided to the user through a visual output means, such as a display, using various visual methods or may be provided through a speaker and/or a haptic motor using a non-visual method, such as voice, tactile sensation, vibration, or the like.

Figure 6A:
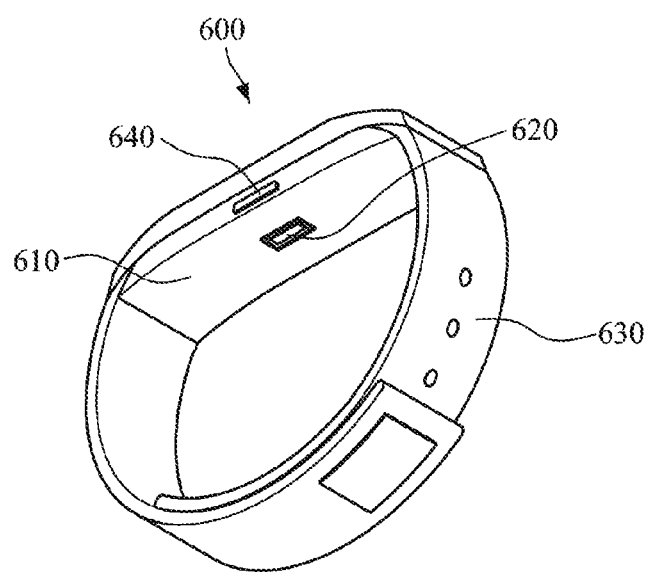
FIGS. 6A and 6B are diagrams illustrating a wearable device.
Figure 6B:
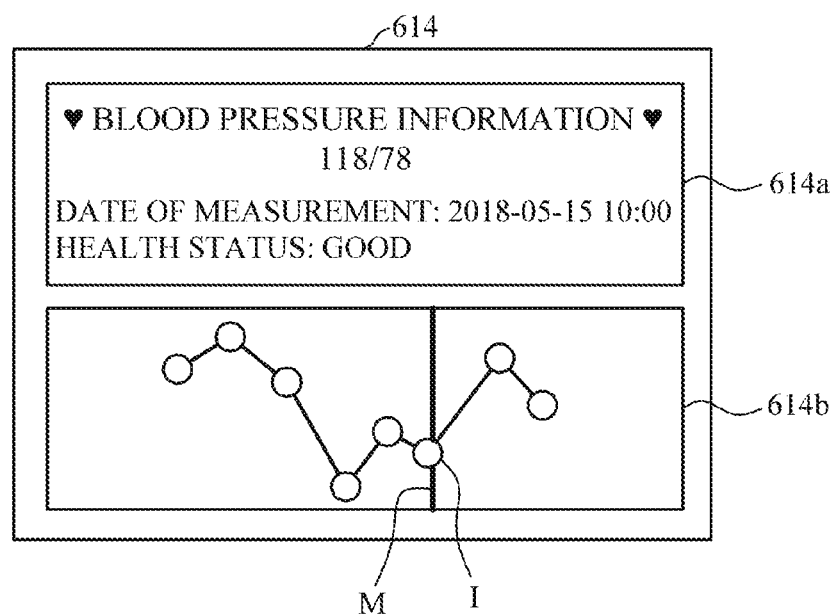

FIGS. 6A and 6B are diagrams illustrating a wearable device. The above-described embodiments of the apparatuses 100a and 100b for estimating blood pressure may be mounted in a smartwatch worn on a wrist or a smart band-type wearable device. However, this is merely an example for convenience of description and the embodiments may be applied to an information processing terminal, such as a smartphone, a tablet PC, a laptop PC, a desktop PC, or the like.

Referring to FIGS. 6A and 6B, the wearable device 600 may include a device main body 610 and a strap 630.

The main body 610 may be formed in various shapes and modules for performing the above-described function of blood pressure estimation and other various functions may be mounted inside or on the surface thereof. A battery for providing power to various modules of the device 600 may be embedded in the main body 610 or the strap 630.

The strap 630 may be connected to the main body 610. The strap 630 may be formed to be flexible so as to be bent in a shape to wrap around a wrist of a user. The strap 630 may be configured in a form that is detached from the user's wrist or be configured in the form of an undivided band. The strap 630 may be filled with air or have an air bag to have elasticity according to a change in pressure applied to the wrist and may transmit the pressure change of the wrist to the main body 610.

A sensor 620 configured to measure a bio-signal may be mounted in the main body 610. The sensor 620 may be mounted on a rear surface of the main body 610 that is brought into contact with an upper part of the wrist of the user and the sensor 620 may include a light source configured to emit light to the skin of the wrist and a detector configured to detect light scattered or reflected from an object of interest. The sensor 620 may further include a contact pressure sensor configured to measure a contact pressure exerted by the object of interest.

A processor may be mounted in the main body 610 and may be electrically connected to various configurations mounted in the wearable device 600 to control the configurations.

In addition, the processor may estimate blood pressure using a bio-signal measured by the sensor 620. The processor may acquire a first feature value associated with CO and a second feature value associated with TPR from the bio-signal. In addition, the processor may normalize the first feature value and the second feature value respectively to a first reference value and a second reference value at the time of calibration so as to obtain a first normalization value and a second normalization value. In addition, the processor may acquire a first variation relative to the time of calibration and a second variation relative to the time of calibration for the first normalization value and the second normalization value and may estimate blood pressure by combining the acquired first variation and second variation.

Meanwhile, the processor may determine, by using the acquired values, whether the mechanism of blood pressure change is a mechanism of low blood pressure. For example, when a difference between the first normalization value and the second normalization value is greater than a first threshold, the second normalization value is smaller than a second threshold, and the second feature value is smaller than a third threshold, the mechanism of blood pressure change may be determined to be the mechanism of low blood pressure. However, the embodiment is not limited thereto.

When the determined mechanism of blood pressure change is a general mechanism of blood pressure change, the processor may estimate blood pressure by combining the first feature value and the second feature value intact as shown in Equation 1 above. When the mechanism of blood pressure change is the mechanism of low blood pressure, an offset value for correcting an error between the estimated blood pressure and the actual blood pressure in accordance with the mechanism of low blood pressure may be further acquired and the blood pressure may be estimated by further combining the offset value with the first and second variations as shown in Equation 4 above.

In a case in which a contact pressure sensor is mounted, the processor may monitor a contact state of the object of interest based on a contact pressure between the wrist and the sensor 620 and provide guidance on a contact position and/or a contact state to the user through a display.

In addition, a storage in which a processing result of the processor and a variety of information are stored may be mounted in the main body 610. The variety of information may include reference information for estimating blood pressure and other information associated with functions of the wearable device 600.

In addition, an operator 640 configured to receive a user's control command and transmit the control command to the processor may be mounted in the main body 610. The operator 640 may include a power button for the user to input a command for powering on/off the wearable device 600.

A display 614 may be mounted on a front surface of the main body 610 and may include a touch panel capable of receiving a touch input. The display 614 may receive the user's touch input, transmit the touch input to the processor, and display a processing result of the processor.

For example, the display 614 may display estimated blood pressure information. In this case, additional information, such as date of estimation of blood pressure or health status, may be displayed together with the estimated blood pressure information. At this time, when the user requests detailed information by operating the operator 640 or through touch input to the display 614, the detailed information may be output in various ways.

Referring to FIG. 6B, the display 614 may output the detailed information in a first region 614a and output a blood pressure history graph in a second region 614b. In this case, the blood pressure history graph may include an object (e.g., a figure, such as a circle, a rectangle, or the like) indicating the time of blood pressure estimation. In addition, an identification mark M that indicates an object I currently selected by the user may be displayed on the blood pressure history graph. Although the identification mark I is illustrated as a vertical line, the embodiment is not limited thereto and the identification mark I may be displayed in various forms, such as a circle, a polygon, such as a rectangle, an arrow indicating a pertinent position, and the like. The user may request the display of the blood pressure history graph. When the blood pressure graph is displayed in the second region 614b, the user may touch an object I at a specific point in time or move the graph to the left or right to match the object I at the specific point in time to the identification mark M so that the detailed information can be output in the first region 614a. In this case, information, such as a blood pressure estimate value at the time of estimation selected by the user, the estimation date, and the health status at the pertinent point in time may be output to the first region 614a. However, the embodiment is not limited to the above example.

In addition, a communication interface configured to communicate with an external device, such as a portable terminal of the user, may be mounted in the main body 610. The communication interface may transmit a result of estimation of bio-information to the external device, for example, a smartphone of the user, and allow the result to be displayed to the user. However, the embodiment is not limited thereto and a variety of necessary information may be transmitted and received.

Figure 7:
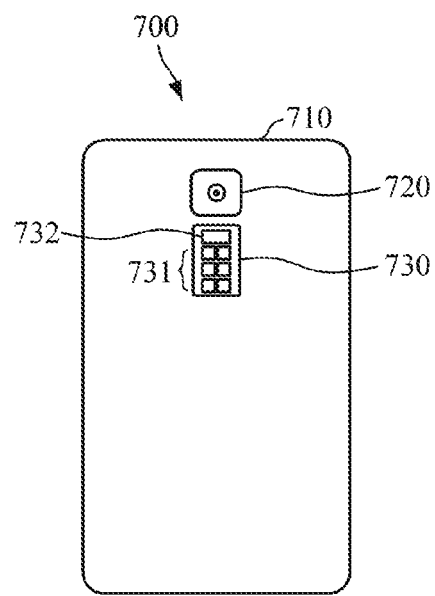
FIG. 7 is a diagram illustrating a smart device.

FIG. 7 is a diagram illustrating a smart device to which embodiments of an apparatus for estimating blood pressure are applied. In this case, the smart device may include a smartphone, a tablet PC, and the like.

Referring to FIG. 7, the smart device 700 may have a sensor 730 mounted on one side of a main body 710. The sensor 730 may include a pulse wave sensor having one or more light sources 731 and a detector 732. As shown in FIG. 7, the sensor 730 may be mounted on a rear surface of the main body 710 but is not limited thereto, and the sensor 730 may be combined with a fingerprint sensor or a touch panel on a front surface.

In addition, a display may be mounted on the front surface of the main body 710. The display may visually output a result of estimation of bio-information and the like. The display may include a touch panel, receive a variety of information input through the touch panel, and transmit the received information to a processor.

Meanwhile, an image sensor 720 may be mounted in the main body 710. When a finger of the user approaches the sensor 730 in order to measure a pulse wave signal, the image sensor 720 may capture an image of the finger and transmit the image to the processor. In this case, the processor may recognize a relative position of the finger with respect to an actual position of the sensor 730 from the image of the finger and provide information on the relative position of the finger to the user through the display, thereby guiding the user to more accurately measure a pulse wave signal.

The processor may estimate blood pressure using a bio-signal measured by the sensor 730. The processor may determine whether a mechanism of blood pressure change is a general mechanism of blood pressure change or a mechanism of low blood pressure, and may estimate blood pressure using a suitable method according to the determined mechanism of blood pressure change. For example, when a difference between the above-described first normalization value associated with CO and the above-described second normalization value associated with TPR is greater than a first threshold, the second normalization value is smaller than a second threshold, and the second feature value is smaller than a third threshold, the processor may determine that the mechanism of blood pressure change is the mechanism of low blood pressure. However, the embodiment is not limited thereto.

When the determined mechanism of blood pressure change is the general mechanism of blood pressure change, the processor may estimate blood pressure by combining a first variation and a second variation intact as shown in Equation 1 above. When the mechanism of blood pressure change is determined to be the mechanism of low blood pressure, the processor may appropriately adjust the first variation and/or the second variation using the above-described method and then estimate blood pressure by combining the adjusted first variation and second variation as shown in Equation 3 above. For example, the first variation may be adjusted after an attenuation coefficient may be obtained using an attenuation coefficient calculation formula, as shown in FIG. 3B, and the second variation may not be adjusted by setting an amplification factor to 1. However, the embodiment is not limited thereto.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating blood pressure, the apparatus comprising:
   a sensor configured to measure a bio-signal from a subject; and
   a processor configured to:
   acquire, from the bio-signal, a cardiac output (CO) feature and a total peripheral resistance (TPR) feature;
   determine that a current mechanism of blood pressure change of the subject is a post-exercise hypotension mechanism based on a variation of the CO feature and a variation of the TPR feature;
   estimate blood pressure based on the variation of the CO feature and the variation of the TPR feature, in response to the current mechanism of blood pressure change not corresponding to the post-exercise hypotension mechanism at a first time point; and
   in response to the current mechanism of blood pressure change corresponding to the post-exercise hypotension mechanism at a second time point, obtain an attenuation coefficient and an amplification factor based on a difference between the CO feature and the TPR feature, decrease the variation of the CO feature by applying the attenuation coefficient to the variation of the CO feature, increase the variation of the TPR feature by applying the amplification factor to the variation of the TPR feature, and estimate the blood pressure based on the decreased variation of the CO feature and the increased variation of the TPR feature, wherein the attenuation coefficient non-linearly decreases from a first value to a second value over time, and subsequently maintains the second value, and wherein the amplification factor non-linearly increases from the first value to a third value over time, and subsequently maintains the third value; and
   a display configured to display a blood pressure history graph that shows the blood pressure that is measured at the first time point when the subject is not in the post-exercise hypotension mechanism, and the blood pressure that is measured at the second time point when the subject is in the post-exercise hypotension mechanism, display graphic objects on the blood pressure history graph at the first time point and at the second time point, and display an identification mark that is movable in a lateral direction to be positioned at one of the graphic objects,
   wherein the processor is further configured to control the display to provide information of the estimated blood pressure corresponding to a location of the identification mark.

2. The apparatus of claim 1, wherein the processor is further configured to:
   determine a heart rate identified from the bio-signal as the CO feature, and determine an amplitude ratio of pulse waveform components constituting the bio-signal as the TPR feature.

3. The apparatus of claim 1, wherein the processor is further configured to:
   determine a heart rate of the subject from the bio-signal and determine an amplitude ratio of pulse waveform components constituting the bio-signal,
   determine a normalization value of the heart rate as the CO feature and determine a normalization value of the amplitude ratio as the TPR feature, and
   wherein when a difference between the normalization value of the heart rate and the normalization value of the TPR feature is greater than a first threshold, the normalization value of the amplitude ratio is smaller than a second threshold and the of the amplitude ratio is smaller than a third threshold, the processor is further configured to determine that the current mechanism of blood pressure change is the post-exercise hypotension mechanism.

4. The apparatus of claim 1, wherein the processor is further configured to:
   determine a normalization value of a heart rate of the subject from the bio-signal and determine a normalization value of an amplitude ratio of pulse waveform components constituting the bio-signal, and
   determine the normalization value of the heart rate as the CO feature and determine the normalization value of the amplitude ratio as the TPR feature,
   wherein when the normalization value of the heart rate is greater than a fourth threshold and the normalization value of the amplitude ratio is smaller than a fifth threshold, the processor is further configured to determine that the current mechanism of blood pressure change is the post-exercise hypotension mechanism.

5. The apparatus of claim 1, wherein the processor is further configured to:
   determine a heart rate of the subject or a normalization value of the heart rate from the bio-signal, and
   determine the heart rate or the normalization value of the heart rate as the CO feature,
   wherein when the heart rate or the normalization value of the heart rate is greater than a sixth threshold, the processor is further configured to determine that the current mechanism of blood pressure change is the post-exercise hypotension mechanism.

6. The apparatus of claim 3, wherein the processor is further configured to obtain the normalization value of the heart rate by dividing the heart rate by a reference heart rate that is measured at a calibration time, and obtain the normalization value of the amplitude ratio by dividing the amplitude ratio by a reference amplitude ratio that is measured at the calibration time.

7. The apparatus of claim 1, wherein the processor is further configured to acquire the CO feature and the TPR feature based on time and amplitude at a maximum point, time and amplitude at a minimum point, or an area under a waveform of the bio-signal.

8. The apparatus of claim 1, wherein the processor is further configured to calculate the variation of the CO feature based on a difference between the CO feature and a reference CO feature obtained at a calibration time, and calculate the variation of the TPR feature based on a difference between the TPR feature and a reference TPR feature obtained at the calibration time.

9. The apparatus of claim 1, wherein, in response to determining that the current mechanism of blood pressure change is not the post-exercise hypotension mechanism, the processor is further configured to estimate the blood pressure based on a combination of the variation of the CO feature and the variation of the TPR feature.

10. The apparatus of claim 1, wherein the attenuation coefficient decreases when at least one of the CO feature, the TPR feature, and the difference between the CO feature and the TPR feature changes.

11. The apparatus of claim 1, wherein the amplification factor increases when at least one of the CO feature, the TPR feature, and the difference between the CO feature and the TPR feature changes.

* * * * *